United States Patent [19]

Bittner

[11] Patent Number: 4,843,006
[45] Date of Patent: Jun. 27, 1989

[54] RECA PROMOTER DEPENDENT POLYPEPTIDE PRODUCTION

[75] Inventor: Michael L. Bittner, St. Louis, Mo.

[73] Assignee: Monsanto Company, St. Louis, Mo.

[21] Appl. No.: 856,850

[22] Filed: Apr. 21, 1986

Related U.S. Application Data

[63] Continuation of Ser. No. 523,254, Aug. 15, 1983, abandoned, which is a continuation-in-part of Ser. No. 436,209, Oct. 25, 1982, abandoned.

[51] Int. Cl.[4] ............... C12N 15/00; C12P 21/00; C07H 15/12
[52] U.S. Cl. ................... 435/172.3; 435/68; 435/320; 536/27; 935/29; 935/41; 935/47
[58] Field of Search ............ 435/68, 172.3, 317, 435/435, 320; 536/27; 935/29, 41, 47, 56, 73

[56] References Cited

U.S. PATENT DOCUMENTS 4,366,246 12/1982 Riggs ............... 435/68

OTHER PUBLICATIONS

Miki et al. 1981 "Construction of a Fused Operon Consisting of the recA and Kan(Kanamycin Resistance) Genes and Regulation of its Expression . . . " Mol. Gen. Genet. v 183, pp. 25–31.

Feinstein et al 1983 "Expression of Human Interferon Genes using the recA promoter of E.coli" Nucleic Acids Research v11(9) 2927–2941.

Casaregola et al 1982 "Quantitative Expression of recA Gene Expression in E. coli" Mol Gen Genet v 185 430–39.

Eitner et al., 1982 "Interspecies recA Protein Substitution in E. coli and Proteus mirabilis" Mol Gen Gen v 185 481–86.

Beck et al 1982 "Nucleotide Sequence and Exact Localization of the Neomycin Phosphotransferase Gene from Tn5" Gene v19 527–36.

Primary Examiner—Charles F. Warren
Assistant Examiner—David T. Fox
Attorney, Agent, or Firm—D. R. Hoerner, Jr.; L. R. Swaney; J. W. Williams, Jr.

[57] ABSTRACT

This invention relates to the expression and accumulation in bacterial cells of heterologous polypeptides under the control of the recA promoter/operator region. One such polypeptide comprises a recA/somatostatin fusion polypeptide. This fusion polypeptide has been expressed and accumulated by E. coli with much greater effectiveness than other somatostatin-containing fusion polypeptides. In addition, use of the recA promoter/opeerator region provides greater induction flexibility than other inducible promoter systems.

2 Claims, 8 Drawing Sheets

```
         (recA)              EcoRI              (somatostatin)
DNA ----- TCA CTG GAA TTC ATG GCT --------
PROTEIN-- Ser Leu* Glu Phe Met Ala --------
```
(* 48th amino acid of recA protein)

```
         (recA)           EcoRI        (somatostatin)
DNA ----CTG AGC GAA TTC ATG GCT-----
PROTEIN --Leu Ser*Glu Phe Met Ala------
         (*330th amino acid of recA protein)
```

RECA PROMOTER DEPENDENT POLYPEPTIDE PRODUCTION

RELATED APPLICATION

This is a continuation of application Ser. No. 523,254, filed Aug. 15, 1983, now abandoned, is a continuation-in-part of U.S. application Ser. No. 436,209, filed on Oct. 25, 1982.

TECHNICAL FIELD

This invention is in the fields of genetic engineering and bacterial expression of mammalian protein.

BACKGROUND OF THE INVENTION

It is possible through the techniques of genetic engineering to cause a host cell to create "heterologous" polypeptides, i.e., polypeptides which are not naturally created by that species of cell. A variety of mammalian polypeptides have been produced in *E. coli* cells, such as somatostatin, described by Itakura et al, *Science* 198: 105 (1977); the component A and B chains of human insulin, disclosed by Goeddel et al, *Proc. Nat'l. Acad. Sci. USA* 76: 106 (1979); human growth hormone, disclosed by Goeddel et al, *Nature* 281: 544 (1979); human leukocyte interferon, disclosed by Goeddel et al, *Nature* 287: 411 (1980); human fibroblast interferon, disclosed by Goeddel et al *Nucleic Acids Res.* 8 (18): 4057 (1980); and human serum albumin, as disclosed by Lawn et al, *Nucleic Acids Res.* 9(22): 6103 (1981).

In order to cause a host cell to express a heterologous polypeptide, a structural sequence (also commonly called a coding sequence) which codes for a polypeptide is usually placed near a promoter sequence which causes the structural sequence to be transcribed into messenger RNA (mRNA). A variety of promoter sequences have been used to promote the expression of chimeric genes in *E. coli*, such as the lac promoter, Backman and Ptashne, *Cell* 13: 65 (1978); the trp promoter, Hallewell and Emtage, *Gene* 9: 27 (1980); and the phage lambda $P_L$ promoter, Bernard et al, *Gene* 5: 59 (1979).

A variety of gene promoter/operator systems are "inducible"; their activity can be varied substantially by the presence or absence of a certain substance or condition. For example, the lac promoter system of *E. coli* has a relatively low level of activity in the absence of lactose, a particular type of sugar molecule. However, in the presence of lactose (i.e., when lactose is added to the culture medium which contains the *E. coli* cells), the lac promoter system becomes much more active, and causes a higher level of transcription of the DNA sequence near the promoter. See, e.g., J. Miller and W. Reznikoff, *The Operon*, 2nd edition, Cold Spring Harbor Labs, N.Y. (1982). Other inducible promoter systems include the trp promoter (which has relatively low activity if an excess of tryptophan is present, and higher activity if a low concentration of tryptophan is present or if 3 B-indolylacrylic acid is present; see Hallewell and Emtage, supra) and the phage lambda promoter (which has a relatively low level of activity at 37° C. and higher activity at 42° C. in the presence of a temperature-sensitive mutant lambda repressor; see Bernard, supra).

The recA gene of *E. coli* has been cloned and its nucleotide sequence has been reported; see T. Horii et al, "Organization of the recA gene of *E. coli*," *P.N.A.S. USA* 77:313 (1980) and A. Sancar et al, "Sequences of the recA gene and protein," *P.N.A.S. USA* 77:2611 (1980). The recA polypeptide is involved in a variety of functions, including genetic recombination and a class of functions called "SOS" functions which occur when the cell is placed under certain types of stress. The recA polypeptide is commercially available from P-L Biochemicals, Inc. (Milwaukee, Wis.). Expression of the recA gene can be induced by a variety of substances including nalidixic acid and mitomycin C, and by various stress conditions such as ultraviolet radiation. See E. M. Witkin, "Ultraviolet mutagenesis and inducible DNA repair in *E. coli*," *Bacteriol. Rev.* 40:869 (1976). If appropriate mutant host cells are used, then certain other stress conditions, such as elevated temperature or thymine starvation, may be used to induce expression of the recA polypeptide.

Prior to the filing of the parent application in this case, there had been two reports of the use of a recA promoter in a man-made chimeric gene. The first report, T. Miki et al, "Construction of a Fused Operon Consisting of the recA and kan (Kanamycin Resistance) Genes and Regulation of Its Expression by the lexA Gene," *Mol. Gen. Genet.* 183: 25–31 (1981), discussed the use of a recA promoter to promote transcription of a structural sequence which was translated into the enzyme, kanamycin phosphotransferase (KPT). KPT inactivates kanamycin, an antibiotic which is toxic to *E. coli* cells. KPT is naturally present in various strains of *E. coli* which contain certain plasmids or transposons; in the presence of kanamycin, the KPT gene can serve as a selectable marker. The apparent purpose of the work reported by Miki, et al was to evaluate the interrelationship between the recA gene and a different gene, designated the lexA gene, which produces a protein called lexA which represses transcription of the recA gene.

The second report, S. Casaregola et al, "Quantitative Evaluation of recA Gene Expression in *E. coli*," *Mol. Gen. Genet.* 185: 430–439 (1982), involved a recA::lac chimeric gene. Since the different enzymatic activities of the recA protein are difficult to measure, Casaregola et al created a chimeric gene comprising a structural sequence which is translated into beta-galactosidase (B-gal), controlled by a recA promoter. B-gal is an enzyme that is naturally present in various strains of *E. coli*.

In addition, one report was published in 1983 after the parent application was filed. This report, by S. I. Feinstein et al, *Nucleic Acids Research* 11(9): 2927–2941 (1983), describes the use of the recA promoter to express human interferon genes in *E. coli*.

As used herein, the term "endogenous polypeptide" refers to a polypeptide that exists naturally in a certain genus or species of host cells. For example, some naturally occurring strains of *E. coli* contain an enzyme, having kananycin phosphotransferase (KPT). Therefore, even though not all strains of *E. coli* contain KPT, it may be regarded as endogenous with respect to cells of the species *E. coli*. By comparison, the term "heterologous polypeptide", as used herein, refers to a polypeptide that does not naturally exist in a genus or species of host cells. For example, a mammalian or plant polypeptide would be regarded as heterologous with respect to *E. coli* and other bacterial cells.

It is normally much easier to cause the expression by a chimeric gene of an endogenous polypeptide in a certain type of bacterial host cell (such as KPT or B-galactosidase, both of which naturally exist in some strains of *E. coli* cells) than to cause a bacterial host cell to express a heterologous polypeptide, such as interferon or somatostatin. This is due to a variety of complex processes which are not completely understood. Some of the factors which are believed to impede the expression or accumulation of a heterologous polypeptide in a host cell include the following:

1. the heterologous polypeptide may be degraded by the host cell.

2. the heterologous polypeptide may have toxic effects upon the host cell, presumably because of interaction with one or more naturally occurring proteins or other substances which are essential to the functioning of the cell.

The problem of degradation is believed to be more severe with regard to relatively small heterologous polypeptides than with regard to large heterologous polypeptides. Although a wide variety of heterologous polypeptides with more than about 100 amino acid residues have been expressed in *E. coli*, relatively few heterologous polypeptides with less than about 50 amino acid residues have been expressed in *E. coli*, despite numerous attempts to do so.

A number of efforts to overcome the problems of causing heterologous polypeptides to be expressed in bacterial cells have utilized "fusion" polypeptides. Such fusion polypeptide normally utilize a portion of a naturally occurring *E. coli* polypeptide (often called a "carrier" polypeptide) coupled to a polypeptide selected by the investigator. Such fusion polypeptides are usually created by inserting a heterologous structural sequence into the structural sequence of a selected *E. coli* gene. The inserted structural sequence is transcribed into chimeric mRNA under the control of the promoter/operator sequence of the *E. coli* gene, and the chimeric mRNA is translated into a polypeptide under the control of the 5' non-translated region and the AUG start codon of the *E. coli* gene. In a fusion polypeptide, the inserted structural sequence must be in the proper reading frame relative to the AUG start codon of the *E. coli* gene. See e.g., Goeddel et al *P.N.A.S.* (1979), supra, and U.K. Patent Application GB No. 2,007,676A (Itakura and Riggs, publ. 1979).

Despite these and other technological advances, various problems continue to limit the range or utility of efforts to use *E. coli* cells to express certain heterologous polypeptides, such as somatostatin. Such problems include:

1. expression of the heterologous polypeptide even while the promoter is repressed. This tends to slow down or divert other metabolic and reproductive processes which are more useful during the growth phase. This reduces the number or vitality of host cells that can be grown in a certain amount of time, thereby reducing the amount of heterologous polypeptide which can be expressed and accumulated by the cells during a time-limited fermentation cycle.

2. lack of adequate flexibility in the control of a promoter/operator system. Most known promoter/operator systems can be induced effectively by only one or a few known substances or conditions. However, any particular inducing substance or condition may have other deleterious effects upon a particular strain of host cells or a particular metabolic reaction. It would be preferable to have a promoter system which can be induced by a wide variety of substances or conditions.

3. for reasons which are not yet understood, certain heterologous polypeptides have apparent detrimental effects upon certain cells. This is usually manifested by several effects, such as:

a. difficulties encountered by researchers who are attempting to isolate cells containing plasmids that would be expected to result from specific DNA manipulative efforts, and b. plasmid instability. For example, Itakura et al report that the plasmids they created which contain a chimeric B-gal/somatostatin gene was relatively unstable; see Itakura et al, *Science* 198: 1056 at 1062 (1977). A relatively minor degree of plasmid instability, expressed over a large number of generations, can lead to a very large subpopulation which does not express the desired polypeptide, if the absence of the polypeptide confers a reproductive advantage upon the subpopulation.

Although Itakura et al, supra, have reported the expression of a fusion polypeptide containing somatostatin coupled to part of a B-gal polypeptide from *E. coli*, their paper discusses several limitations on the efficient expression of that fusion polypeptide in *E. coli*, including plasmid instability and low levels of accumulation within the host cells. Efforts by Monsanto scientists to create similar plasmids have confirmed that similar problems do (described below) do in fact prevent the accumulation of desirable levels of B-gal/somatostatin fusion polypeptides in *E. coli*.

SUMMARY OF THE INVENTION

This invention relates to the expression and accumulation in bacterial cells of heterologous polypeptides (i.e., polypeptides which are not naturally produced by *E. coli* cells) that are expressed under the control of the recA promoter/operator region.

This invention also relates to chimeric genes and cloning vectors which utilize the recA promoter/operator region, and to heterologous polypeptides which are created by means of this invention. One such heterologous polypeptide comprises a fusion polypeptide with the amino acid sequence of the recA polypeptide at its amino terminus, and the somatostatin sequence at its carboxy terminus. This fusion polypeptide has been shown to be expressed and accumulated with substantially greater ease and effectiveness than the only other reported somatostatin-containing fusion polypeptide, a B-galactosidase/somatostatin fusion.

This invention also discloses control of the repression and induction of the expression of a heterologous polypeptide by means of a variety of chemicals and other conditions. Experimental data is supplied which reports that the expression of heterologous polypeptides under the control of the recA system has been induced by nalidixic acid, mitomycin C, and ultraviolet radiation. It is also believed that expression can be induced in appropriate host cells by various other conditions which impede DNA replication, such as elevated temperatures and thymine starvation. The variety of inducing substances and conditions provides several advantages in efforts to cause cells to express and accumulate heterologous polypeptides.

In the plasmids shown in FIGS. 1 to 5, the arrows indicate direction of translation.

DETAILED DESCRIPTION OF THE INVENTION

In one embodiment of this invention, the Applicant synthesized an oligonucleotide which contained an EcoRI terminus, codons for 15 amino acids (methionine and the 14 amino acids of natural somatostatin) and a SalI terminus. This oligonucleotide was inserted into plasmid pBR327 (citations to articles describing relevant plasmids are contained in the examples) which had been digested with EcoRI and SalI, to obtain plasmid pMON1004. This plasmid was then modified by inserting an oligonucleotide into the unique SalI cleavage site, to create a new BamHI cleavage site next to the SalI site. The resulting plasmid was designated as pMON2003, as shown on FIG. 1. This procedure is described in more detail in Example 2.

Figure 1:
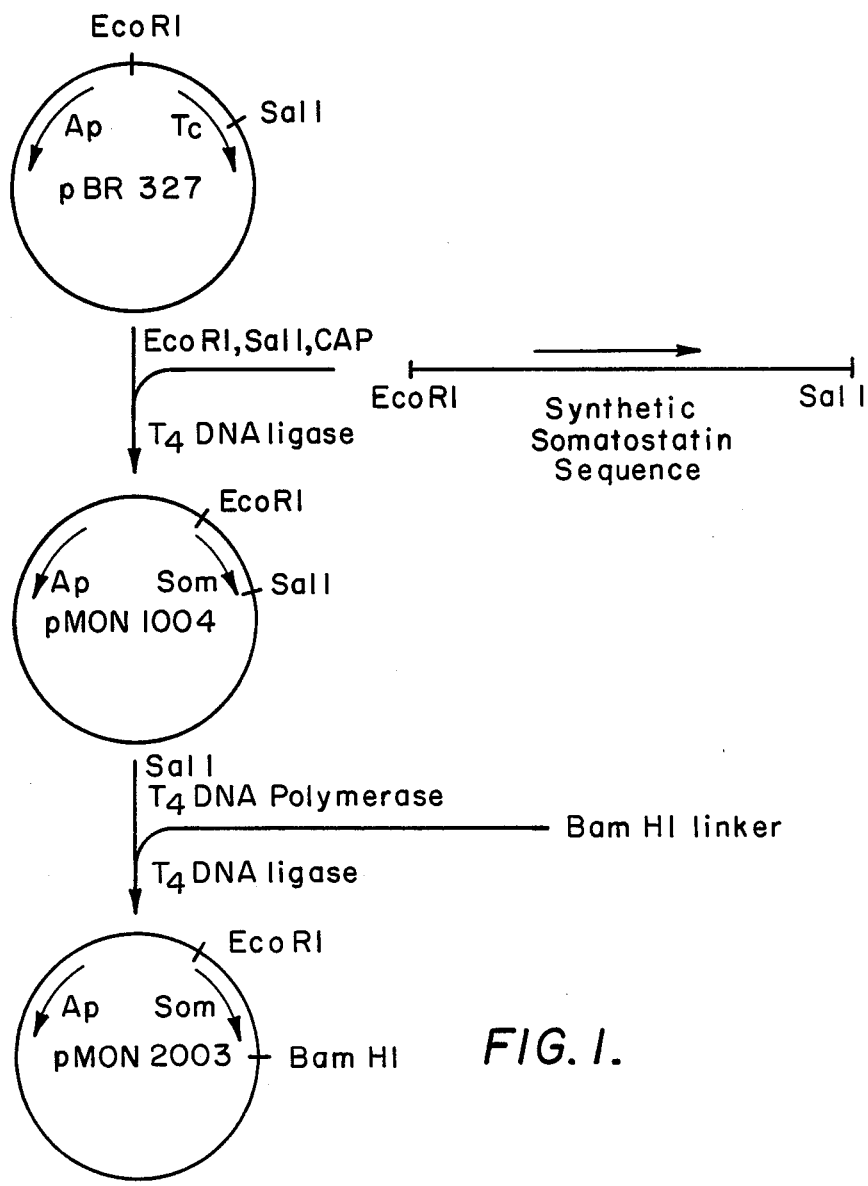
FIG. 1 illustrates the construction of plasmid pMON2003, which contains a structural sequence for somatostatin bounded by EcoRI and BamHI cleavage sites.
Figure 2:
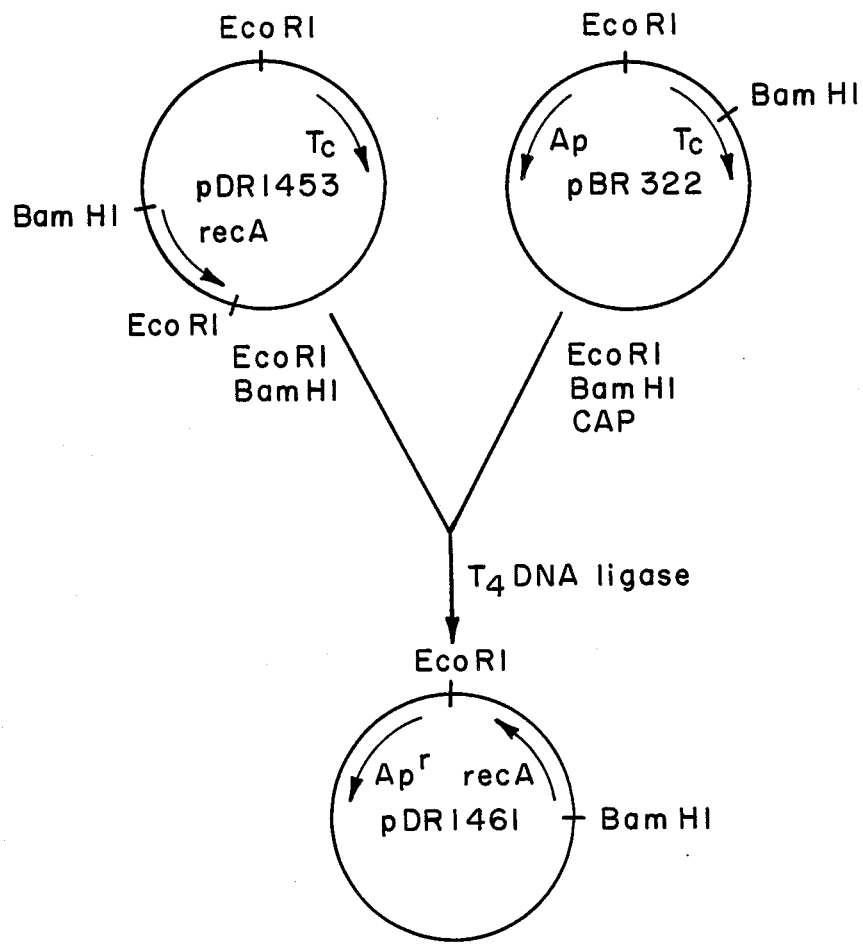
FIG. 2 illustrates the construction of plasmid pDR1461, which contains the recA promoter/operator region bounded by EcoRI and BamHI cleavage sites.

Plasmid pDR1453, which contains an entire recA gene was received as a gift from Dr. W. Dean Rupp of Yale School of Medicine. The Applicant digested this plasmid with two endonucleases, EcoRI and BamHI, to obtain a linearized gene fragment. This fragment contained (in 5' to 3' sequence on the sense strand) a BamHI terminus, the recA promoter/operator region, a 5' non-translated region (which includes a ribosome binding site), part of the recA structural sequence (including the ATG start codon), and an EcoRI terminus. The Applicant inserted this fragment into plasmid pBR322, which had been digested with EcoRI and BamHI, to obtain plasmid pDR1461, as shown in FIG. 2. This procedure is described in more detail in Example 3.

The Applicant then mixed plasmids pDR1461 and pMON2003 and linearized each plasmid by digestion with EcoRI. The EcoRI nuclease was inactivated by heat, and T4 DNA ligase was added to the mixture. Although it was possible that any plasmid might religate to itself, it was probable that at least some of the pDR1461 plasmids would ligate to pMON2003 in the desired orientation, which placed the methionine and somatostatin codons from pMON2003 in the same reading frame as the recA codons from pDR1461, as shown in Table 1.

TABLE 1

Sequence of Somatostatin Structural Sequence

| recA | | | | |
|---|---|---|---|---|
| DNA------C A G | G C T | G A A | T T C | A T G |
| protein----- Glu | Ala | Glu | Phe* | Met |
| G C T | G G C | T G T | A A G | A A C |
| Ala+ | Gly | Cys | Lys | Asn |
| T T C | T T C | T G G | A A A | A C C |
| Phe | Phe | Trp | Lys | Thr |
| T T T | A C C | T C T | T G C | T A A |
| Phe | Thr | Ser | Cys | stop |

Bam HI
T A G T C G A C C G G A T C C
stop

*Phe is the 260th amino acid of recA protein
+Ala is the first amino acid of somatostatin As shown above, an ATG codon for methionine was included between the 260th codon of the recA structural sequence (TTC, which codes for phenylalanine) and the first codon of the somatostatin structural sequence (GCT, which codes for alanine). This was done so that the somatostatin polypeptide could be separated from the recA polypeptide if desired, by treating the fusion polypeptide with cyanogen bromide under appropriate conditions.

A variety of other desired amino acid residues or sequences may be provided to allow cleavage of the heterologous polypeptide from the carrier polypeptide. For example, if the heterologous polypeptide contains an internal methionine residue, cleavage of the polypeptide by CNBr in formic acid would cleave the heterologous polypeptide, which may be undesirable. To avoid this, a tryptophan residue may be inserted between the carrier polypepide and the heterologous polypeptide, by means of inserting a UGG codon into the chimeric gene at the appropriate location. It is possible to cleave polypeptides at tryptophan residues (while leaving most methionine residues unaffected) by CNBr treatment under appropriate conditions; see, e.g., H. V. Huang et al, *Methods in Enzymology* 91: 318 (1983). Alternatively, it is possible to insert more than one or more amino acid residues to provide a residue or sequence that can be recognized and cleaved by a proteolytic enzyme, such as trypsin (which cleaves at either lysine or arginine residues), chymotrypsin (which cleaves at tryptophan, phenylalanine, or tyrosine residues), collagenase (which cleaves pro-x-gly-pro sequences), or thrombin (which cleaves proline-arginine sequences).

If one or more amino acids of the heterologous polypeptide may be removed from the polypeptide without adversely affecting the desired characteristics (such as stability and enzymatic activity) of the polypeptide to an unacceptable level, then the cleavage residue or sequence may be located within the heterologous polypeptide.

The ligated mixture of pDR1461 and pMON2003 fragments was digested with BamHI, and ligated with an M13 phage which had also been digested with BamHI. The M13 phage is a virus which goes through both single-stranded and double-stranded stages in its reproductive cycle, making it useful for certain types of DNA manipulations. Various strains of M13 have been prepared which have certain endonuclease cleavage sites, such as M13 mp8, which has a unique BamHI site (and several other unique sites). A variety of M13 mp8 phages were obtained; these were screened for the presence of M13 replicative form (RF) DNA containing a 1.8 kilobase (kb) insert with BamHI ends. Five such clonal colonies were identified; these were further analyzed to determine the orientation of the BamHI inserts. The plasmids from two colonies having different orientations were designated as pMON2004 and pMON2005, as shown on FIG. 3. This procedure is described in more detail in Example 4.

The Applicant subsequently digested pMON2005 with BamHI, purified the 1.8 kb fragment, and ligated it with a separate plasmid, pMOB45, which had also been digested with BamHI. Plasmid pMOB45 has a temperature sensitive replicon which allows a method of increasing the plasmid copy number per cell, and two selectable marker genes (chloramphericol resistance, Cm ®, and tetracycline resistance, Tc ®). The Tc ® gene is disrupted by inserting DNA into the BamHI cleavage site.

Figure 4:
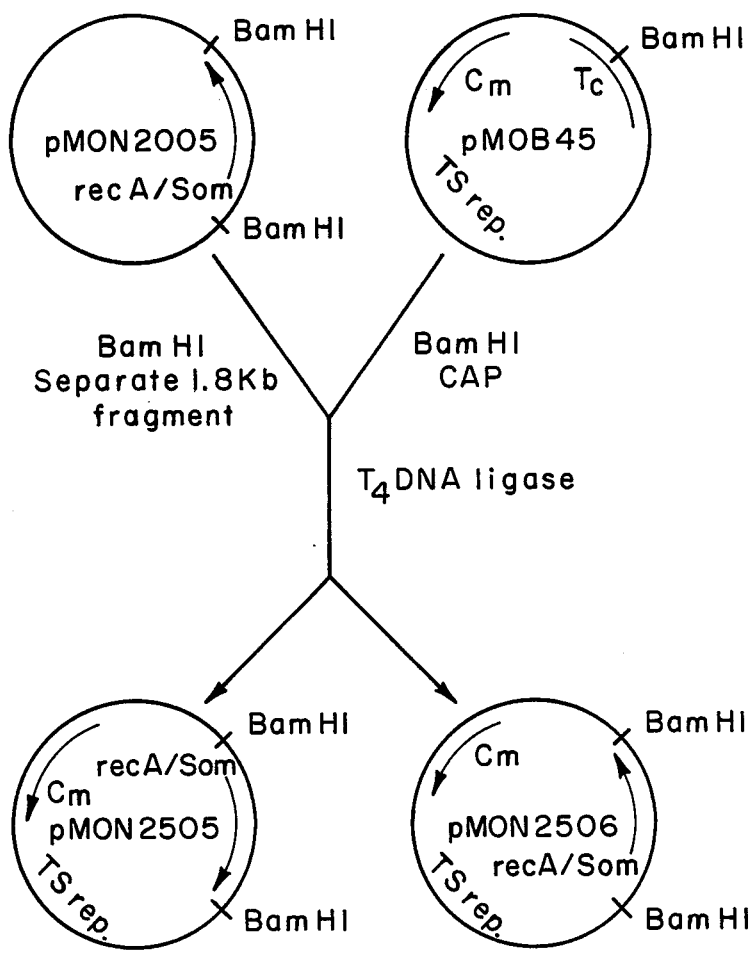
FIG. 4 illustrates the insertion of the recA/somatostatin chimeric gene into pMOB45 (in two different orientations) to create plasmids pMON2506 and pMON2505.

Plasmids were isolated having the recA/somatostatin fragment inserted into pMOB45 in both directions. These plasmids were designated pMON2505 and pMON2506, as shown in FIG. 4. This process is described in more detail in Example 5.

Plasmid pKO-1 contains a promoterless gene (i.e., a structural sequence with start and stop codons and a 3' non-translated region). If this gene is transcribed into mRNA, the mRNA can be translated into galactokinase (gal-K), an enzyme which can be easily assayed. If a chimeric gene with a promoter is inserted into plasmid pKO-1 near the gal-K structural sequence and with the same orientation, the level of expression of gal-K provides additional information on the transcription of the chimeric gene and the stability of the mRNA thus created.

Figure 5:
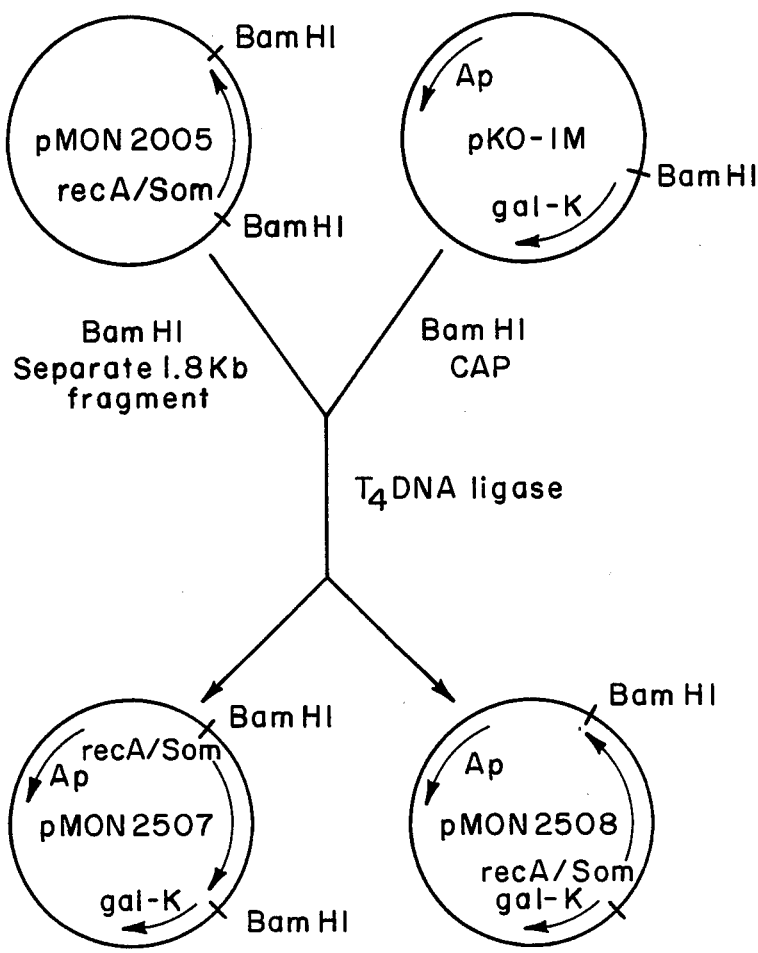
FIG. 5 illustrates the insertion of the recA/somatostatin chimeric gene into pKO-1M (in two different orientations) to create plasmids pMON2508 and 2507.

Plasmid pKO-1M was created by modifying pKO-1 to delete the SmaI cleavage site near the gal-K structural sequence and replace it with an EcoRI cleavage site. This plasmid was then digested with BamHI, and the 1.8 kb recA/somatostatin fragment (obtained by digesting the M13 plasmid, pMON2005, with BamHI) was ligated with the digested pKO-1M. The resulting plasmids, designated pMON2507 and pMON2508, contained the recA/somatostatin insert in both orientations, as shown in FIG. 5. This procedure, and the construction of pKO-1M, are described in more detail in Example 6. Plasmid pMON2507 is gal+ (it creates red colonies on MacConkey indicator plates); this confirms that the orientation of the inserted recA/somatostatin gene is the same as the orientation of the promoterless galactokinase gene in pMON2507. Plasmid pMON2508 is gal−, since the orientation of the inserted gene is opposite from the orientation of the galactokinase gene.

A variety of plasmids were tested for expression of the recA/somatostatin fusion polypeptide. The results are described in Example 7.

Three additional types of plasmids were constructed to test other means of expressing somatostatin. One set of plasmids, described in Example 8, contained structural sequences with varying numbers of recA codons, ranging from 48 codons to 330 codons. It was found that high levels of expression could be obtained for fusion polypeptides containing 260 and 330 recA amino acids (plus 14 somatostatin amino acids), while considerably lower levels of expression were obtained for fusion polypeptides with 48 recA amino acids. Based upon these results, it is believed that a relatively long endogenous polypeptide (with more than about 150 or so amino acid residues) is likely to be a better carrier polypeptide than a relatively short endogenous polypeptide. The preferred length of any particular carrier polypeptide to express and particular heterologous polypeptide may be determined through routine experimentation by those skilled in the art.

A second set of plasmids, described in Example 9, contained chimeric genes with the somatostatin structural sequence fused to a B-gal gene (with an inducible promoter, translation start codon, and varying numbers of B-gal codons) and a chloramphenicol acetyl transferase (CAT) gene. These plasmids indicate that only low levels of expression of B-gal/somatostatin fusion polypeptides could be obtained; these levels of expression were substantially lower than the expression that could be obtained of recA/somatostatin polypeptides. In addition, no expression of CAT/somatostatin could be detected despite diligent efforts.

The third set of plasmids, described in Example 10, contained chimeric genes with the recA promoter, a partial recA structural sequence, and various analogs of a somatostatin structural sequence with codons that were translated into amino acids that differed from the amino acid sequence of somatostatin. A variety of other biologically functional analogs of somatostatin, and methods for creating a wide variety of other such analogs, are known to those skilled in the art. See, for example, U.S. Pat. Nos. 3,904,594 (Guillemin et al, 1975); 4,261,885 (Sakakibara et al, 1981); 4,302,386 (Stevens, 1981); 4,061,607 (Shields, 1977); 4,061,608 (Sarantakis, 1977); 4,146,612 (Veber, 1979), 4,189,426 (Li, 1980), and 4,316,891 (Bohlen et al, 1982). Such analogs may be created using the recA promoter/operator region according to the method of this invention used in combination with other methods and substances known to those skilled in the art.

The chimeric recA/somatostatin gene described herein, and the recA/promoter/operator system which can be used in other genes, is suitable for use in a variety of host cells. Suitable host cells include *E. coli* strain C, which is available from the American Type Culture Collection (ATCC) Rockville, Md., under Accession No. ATCC 13706. Another such suitable host bacteria is *E. coli* K-12 Strain 294, ATCC No. 31446. Suitable host cells should be both recA positive and lexA positive, since both the recA and lexA polypeptides are involved in the repression and induction of the recA promoter.

It is believed that a variety of other types of bacteria are suitable as host cells for the recA/promoter/operator system and chimeric genes which utilize that system. For example, it is known that the recA gene of *E. coli* also functions in *Proteus mirabilis;* see Eitner et al, *Mol. Gen. Genet.* 185: 481 (1982). Other strains of bacteria which may be useful as host cells for the subject invention include strains from the genera Enterobacteriaceae, Erwinia, Shigella, Salmonella and Klebsiella; the suitability of any particular host cell for use with this invention may be determined through routine experimentation by those skilled in the art.

Cultures of *E. coli* Strain K-12 DB1443 containing recA/somatostatin plasmids pMON2506 and pMON2507 described herein have been deposited with the ATCC under the Accession No's. ATCC 39212 and ATCC 39211, respectively. The Applicant has claimed microorganisms having the "relevant characteristics"

of either culture. As used herein, the "relevant characteristics" of a cell culture are limited to those characteristics which make the culture suitable for a use which is disclosed, suggested or made possible by the information contained herein. Numerous characteristics of the culture may be modified by techniques known to those skilled in the art; for example, the cells may be made resistant to a particular antibiotic by insertion of a particular plasmid or gene into the cells, or the recA/somatostatin plasmids might be removed from the designated cells and inserted into a different strain of cells. Such variations are within the scope of this invention, even though they may amount to improvements, which undoubtedly will occur after more researchers gain access to these cell cultures.

It is possible to use the recA/operator region in conjunction with one or more control or structural sequences selected from other genes, using methods and substances known and available to those skilled in the art. For example, it is possible to create a chimeric gene comprising (1) the recA promoter/operator region, (2) a 5' non-translated region derived from a second gene, such as the E. coli consensus sequence described by Scherer et al, Nucleic Acids Research 8 (17): 3895 (1980); (3) a start codon and partial coding sequence taken from a desired gene, such as a selectable or chromogenic marker enzyme which can be modified at the carboxy end without sacrificing the desired characteristic of the enzyme; (4) a desired structural sequence such as a sequence which codes for a carrier polypeptide coupled to somatostatin; (5) a 3' non-translated region from a desired gene; and (6) a transcription terminator if desired.

In addition, it is possible to modify the relative position of the heterologous polypeptide with respect to the carrier polypeptide. For example, a structural sequence which codes for a fusion polypeptide containing the somatostatin sequence at or near the amino terminus, or between two carrier fragments, can be created using methods known to those skilled in the art. Such a structural sequence can be placed under the control of the recA promotor/operator region, using the methods of this invention.

This invention is not limited to the creation of fusion polypeptides. It is possible, according to this invention, to place an entire coding sequence of the heterogeneous polypeptide, with its own start and stop codons, under the control of a recA promoter/operator region. A polypeptide expressed by such a gene in a bacterial cell would be within the scope of this invention.

As used herein, the phrase "recA promoter/operator region" (also referred to as the recA promoter or the recA system) is defined as a single- or double-stranded segment of DNA or RNA having a series of bases (1) substantially as described in Horii et al, supra and/or Sancar et al, supra, or (2) derived from the promoter region that is proximally upstream of a recA structural sequence in an E. coli cell, or to any portion or mutated derivative thereof, which has the capability in suitable host cells of promoting the transcription of a proximal segment of DNA in the presence of one or more appropriate inducing agents, such as nalidixic acid, mitomycin C, ultraviolet radiation, elevated temperature, or thymine starvation. Depending upon the desire of the user, the recA promoter may have a 5' non-translated region and/or a translation start codon derived from the recA gene or from any other desired gene. The recA promoter system may be obtained by a variety of methods, including replication of a publicly available plasmid, isolation of the recA gene from E. coli cells using known techniques, or polynucleotide synthesis based upon a published sequence.

For further information and explanation of "heterologous polypeptide," "recA promoter/operator region," and other terms of art used herein, the reader may refer to recognized texts and review publications in the field, such as Watson, *The Molecular Biology of the Gene,* 3rd ed. (W. A. Benjamin, Inc., 1976); R. E. Glass, *Gene Function: E. coli and its heritable elements* (U. Calif. Press, 1982), and Miller and Reznikoff, supra.

It is believed that a wide variety of other heterologous polypeptides such as, for example, the insulin A and B chains, growth hormones, interferons, serum albumin and other blood proteins, endorphins and other such neuropeptides, thymosin $\alpha_1$, angiotensin I, bradykinin, neurotensin, melanocyte inhibiting factor (MIF), melanocyte stimulating factor (MSF), parathyroid hormone, thyrotropin releasing hormone (TRH), luteinizing hormone releasing hormone (LHRH) as well as other somatostatin analogs such as the $(Tyr^1)$, $(Tyr^11)$, $(Ala^5)$ and $(Val^{10})$ analogs, and the like can be expressed by bacteria using the recA promoter/operator region in accordance with the present invention, using the means described herein in combination with other means known to those skilled in the art.

EXAMPLE 1

Materials and Procedures

Restriction endonucleases were purchased from New England Biolabs, Inc., Beverly, Mass. and Bethesda Research Laboratories, Rockville, Md.

Oligonucleotide linkers were purchased from Collaborative Research Inc., Waltham, Mass.

Bacteriophage $T_4$ DNA polymerase was the gift of C. F. Morris and N. K. Sinha. Its preparation is described by Morris et al., *Proc. Nat'l Acad. Sci. USA* 254: 6787–6796 (1979).

Bacteriophage $T_4$ DNA ligase was prepared substantially according to the method of Murray et al., *J. Mol. Biol.* 132: 493–505 (1979).

Plasmid pBR327, described by Soberon et al. *Gene* 9, 287–305 (1980), was obtained from Dr. Paco Bolivar of the University of Mexico. It is a commonly used laboratory plasmid, which contains an E. coli replicon, ampicillin (Ap) and tetracycline (Tc) resistance genes, and a variety of unique cleavage sites.

Three other plasmids (pDR1453, pMOB45, and pKO-1) which were obtained from outside sources are described in the following examples. A variety of other plasmids and host cells were obtained from various sources, as listed in Table 2. Unless otherwise noted, all E. coli host cells are recA+ and lexA+.

TABLE 2

| Host cell strains (source/publication) | Relevant Phenotype |
|---|---|
| E. coli, JM101(J. Messing et al, Nucleic Acid Research 9:309(1981)) | (lac pro), F' lacI$^q$ Z M15, traD, proC+ |
| E. coli, DB1443 (deposited with pMON2507 as ATCC #39211) | C600, hsd R |
| E. coli, N100K−(obtained from M. Rosenberg of NIH) | recA−, galK− |
| E. coli, M182 (M. Casadaban et al., J. Mol. Biol. 138: 179(1980)) | (lac IPOZY) X74, galK, galU, strA. |
| E. coli SR2 (e.g., C. Yanofsky et al., J. Mol. Bio. 21:313 | Ymel, Sup F |

TABLE 2-continued

| Host cell strains (source/publication) | Relevant Phenotype |
|---|---|
| (1966)) | |
| E. coli 294 (ATCC #31446) | endA, thi, hsr, hsm+ highly transformable |
| Vector/plasmids | |
| M13 mp8 (J. Messing, Third Cleveland Symposium on Macromolecules: Recombinant DNA; ed. A. Walton; Elsevier, Amsterdam, pp 143-153(1981) | M13 containing altered segment of the lac operon |
| λplac5 (J. Miller, Experiments in Molecular Genetics, Cold Spring Harbor Labs, 1972). | specialized lambda transducing phage containing the B-galactosidase promoter, operator and structural gene. |

2X YT broth and Luria agar were prepared as previously described by Miller, "Experiments in Molecular Genetics", Cold Spring Harbor Laboratory, Cold SpringHarbor, N.Y., pp. 431-435 (1972) and supplemented with ampicillin (200 ug/ml), tetracycline (10 ug/ml) or chloramphenicol (100 ug/ml) as required. Galactose MacConkey agar was prepared from Difco dehydrated MacConkey agar, then supplemented with ampicillin (200 ug/ml).

Small quantities of DNA were produced using the alkaline miniscreen technique of Horowicz and Burke, *Nuclei Acids Res.* 9, 2989-2998 (1981). Large quantities of DNA were prepared by a modified alkaline lysis (Horowicz and Burke, supra) followed by hydroxyapatite chromatography (see Coleman et al., *Eur. J. Biochem.* 91, 303-310 (1978). DNA fragments generated by restriction digestion were separated in agarose or polyacrylamide gel slabs with either a tris-acetate (see Hayward and Smith, *J. Mol. Biol.* 63, 383-395 (1972), or a tris-borate buffer system (see Maniatis et al., *Biochem.* 14, 3787-3794 (1975). Size estimates of DNA fragments were based on mobility compared to the HindIII restriction fragments of phage λ DNA and the HaeIII restriction fragments of double-stranded $\phi \times 174$ DNA. Pure fragments were recovered from gels by electroelution of DNA from a gel slice into a dialysis bag submerged in a 1:5 dilution of electrophoresis buffer.

Restriction digests were carried out in H50 buffer (6.6 mM Tris-HCl (pH 8.0), 6.6 mM $MgCl_2$, 50 mM NaCl, 5 mM dithiothreitol) at 37° C. with sufficient enzyme to give complete digestion in one half of the chosen period of incubation. One to five ug of vector DNA was treated with 0.2 units of chromatographically purified calf intestinal alkaline phosphatase (CAP) according to the procedure described by Efstratidis et al., *Nucleic Acids Res.* 4: 4165-4174 (1977), at 37° C. for the final 30 minutes of restriction digestion. Phosphatase activity was eliminated by a 30 minute incubation at 70° C., followed by precipitation with ethanol. Unless CAP was used, endonucleases were inactivated by 70° incubation for five minutes.

Addition of nucleotides to convert cohesive termini to blunt termini was accomplished by incubation of the DNA at 37° in H50 buffer supplemented with 100 umolar each dATP, dGTP, dCTP and dTTP and a 1000-fold excess of $T_4$ DNA polymerase. DNA ligations were carried out in 25 mM Tris-HCl (pH 8.0), 10 mM $MgCl_2$, 10 mM dithiothreitol, 0.2 mM spermidine trichloride, 500 uM ATP at room temperature with an amount of enzyme sufficient to convert 95% of all ligatable ends to covalent joints.

Transformation of *E. coli* JM101 with M13 DNA was carried out by using a $CaCl_2$/heat shock method, according to the procedure described by Cohen et al., *Proc. Nat'l Acad. Sci. USA* 69, 2110-2114 (1972). All other transformations were carried out by Hanahan's cell transformation procedure as described by Maniatis et al., "Molecular Cloning", pp. 254-255, Cold Spring Harbor Laboratory (1982).

To perform polypeptide analyses, one ml samples of cells were harvested by centrifugation, washed with one ml of 50 mM Tris-HCl (pH 8.0), 100 mM NaCl, and resuspended in 1 ml of 70% formic acid with 5 mg/ml cyanogen bromide. Cyanogen bromide cleavage (which cleaves polypeptides at methinonine residues) was allowed to proceed overnight at room temperature. The samples were lyophilized to dryness and then assayed by radioimmunoassay (RIA).

$Tyr^1$-somatostatin was iodinated with $I^{125}$. $I^{125}$-$tyr^1$-SS was purified as described by Patel and Reichlin in *Methods of Hormone RIA*, Jaffe and Behrmen, eds., Academic Press, N.Y. (1979). At each iodination 2.5 ug of $tyr^1$-SS was reacted with 1 mCi of $naI^{125}$ (Amersham Co., III) and passed over a column of Sephadex G-25 (superfine). Fractions corresponding to the monoiodinated form of $tyr^1$-SS were pooled, aliquoted, and stored at −20° C. This material retained the ability to bind to somatostatin antibody for up to six weeks.

Competitive radioimmunoassay for somatostatin was performed using rabbit anti-somatostatin antibodies (anti-SS) obtained from Immunonuclear Corporation (Stillwater, Minn., lot #32101). All reagents were diluted in Borate-BSA buffer (0.1M borate, pH 8.4, 1% BSA) and mixed in 1.5 ml Eppendorf tubes in the following order to a final volume of 400 ul: 100 ul buffer, 100 ul standard dilution of somatostatin or unknown sample, 100 ul of anti-SS (final tube dilution 1:300,000), and 100 ul of $I^{125}$-tyr-SS (10,000 cpm/tube). Contents were mixed gently and incubated overnight at 4° C. On the following day, 20 ul of agarose-linked goat anti-rabbit IgG antibody (Miles Laboratories, Elkhart, Ind.) was added to each tube and the tubes were rotated for 2 hours at room temperature. The tubes were spun in an Eppendort centrifuge for 15 seconds and the supernatant was discarded. The pellets were resuspended in 1 ml of borate buffer and centrifuged again. The radioactivity in the resulting pellet was determined with a Beckman "Gamma 8000" counter. Under the conditions of this assay, the rabbit antibody precipitates 30-40% of the $I^{125}$-$tyr^1$-SS in the absence of added somatostatin. Half-maximum displacement of the bound radioactivity occurs around 15 pg of somatostatin in 400 ul of the assay. The minimum detectable level of somatostatin is around 2 pg. In experiments where high levels of somatostatin were expected, a less sensitive goat antisomatostatin antibody was used. In this case agarose-linked rabbit-anti goat IgG was used as the second antibody.

EXAMPLE 2

Construction of pMON1004 and pMON2003

Plasmid pMON1004 was created by synthesizing two polynucleotides and allowing the two polynucleotides to anneal to each other, as shown below:

```
EcoRI
5': AATTCATGGCTGGCTGAAGAAC...
3':     GTACCGACCGACTTCTTG

...TTCTTCTGGAAAACCTTTACCTCT...
   AAGAAGACCTTTTGGAAATGGAGA

...TCGTAATAG         -3'
   AGCATTATCAGCT     -5'
        SalI
```

These polynucleotides were synthesized by the phosphite procedure described by S. L. Beaucage and M. H. Caruthers, *Tet. Letts.* 22: 1859 (1981), as modified by S. P. Adams et al, *J. Am. Chem. Soc.* 105: 61 (1983). They were annealed by slow cooling from 100° C. to room temperature.

Plasmid pBR327 was digested with EcoRI and SalI and treated with CAP. The CAP was heat-inactivated at 70° C. for 30 minutes, and the resulting mixture was mixed with the annealed polynucleotide mixture. This mixture was ligated with T4 DNA ligase for 8 hours at 37°. The resulting plasmids were used to transform *E. coli* strain SR 2. Ampicillin-resistant, tetracycline-sensitive cells were selected, and analyzed by EcoRI and SalI digestion to confirm the existence of the desired insert. Plasmids having the desired somatostatin-coding insert were designated as pMON1004.

Five pmol of plasmid pMON1004 was digested with endonuclease SalI, and the resulting cohesive termini were converted to blunt ends by $T_4$ DNA polymerase. This material was precipitated with ethanol and 400 pmol of double-stranded oligonucleotide linker with blunt ends containing the BamHI restriction recognition site (dCCGGATCCGG) was ligated to the plasmid DNA in a 20 ul reaction. Two ul of the reaction mix was used to transform *E. coli* K-12 strain SR20 competent cells. (Bale et al, *Mutation Res.* 59, 157–165 (1979); referred to as GM42). Twelve ampicillin-resistant cells were screened for a plasmid containing an EcoRI-BamHI restriction fragment approximately 67 nucleotides in length. A plasmid having the structure shown in FIG. 1 was isolated and designated as pMON2003.

EXAMPLE 3

Construction of pDR1461

Plasmid pDR1453 is a derivative of pBR322 containing the cloned recA gene. It has a molecular length of about 13 kilobases. Its construction is described by Sancer and Rupp, *Proc. Nat'l Acad. Sci.* 76 (7), 3144–3148 (1979). It was obtained as a gift from W. D. Rupp of Yale Medical School.

Plasmid pDR1453 was digested with EcoRI and BamHI. This created 2 fragments, including a 1.8 kb fragment with the recA promoter/operator system and the first 260 codons of the recA structural sequence. 50 fmol of the resulting mixture was ligated to 35 fmol of EcoRI, BamHI digested, CAP-treated plasmid pBR322 in a 15 ul reaction. 5 ul aliquots of the reaction were used to transform *E. coli* K-12 strain DB1443 cells which were plated onto Luria broth plates with ampicillin. Ampicillin-resistant colonies were screened for tetracycline resistance. Two of the $Tc^S$, $Ap^R$ colonies were screened for a plasmid containing the 1.8 kb BamHI-EcoRI recA fragment. A plasmid having the structure presented in FIG. 2 was recovered and designated as a DR1461. The construction of plasmid pDR1461 as above was previously reported by Sancar and Rupp, *Proc. Nat'l Acad. Sci.* 76 (7), 3144–48 (1979).

EXAMPLE 4

Construction of pMON2004

Figure 3:
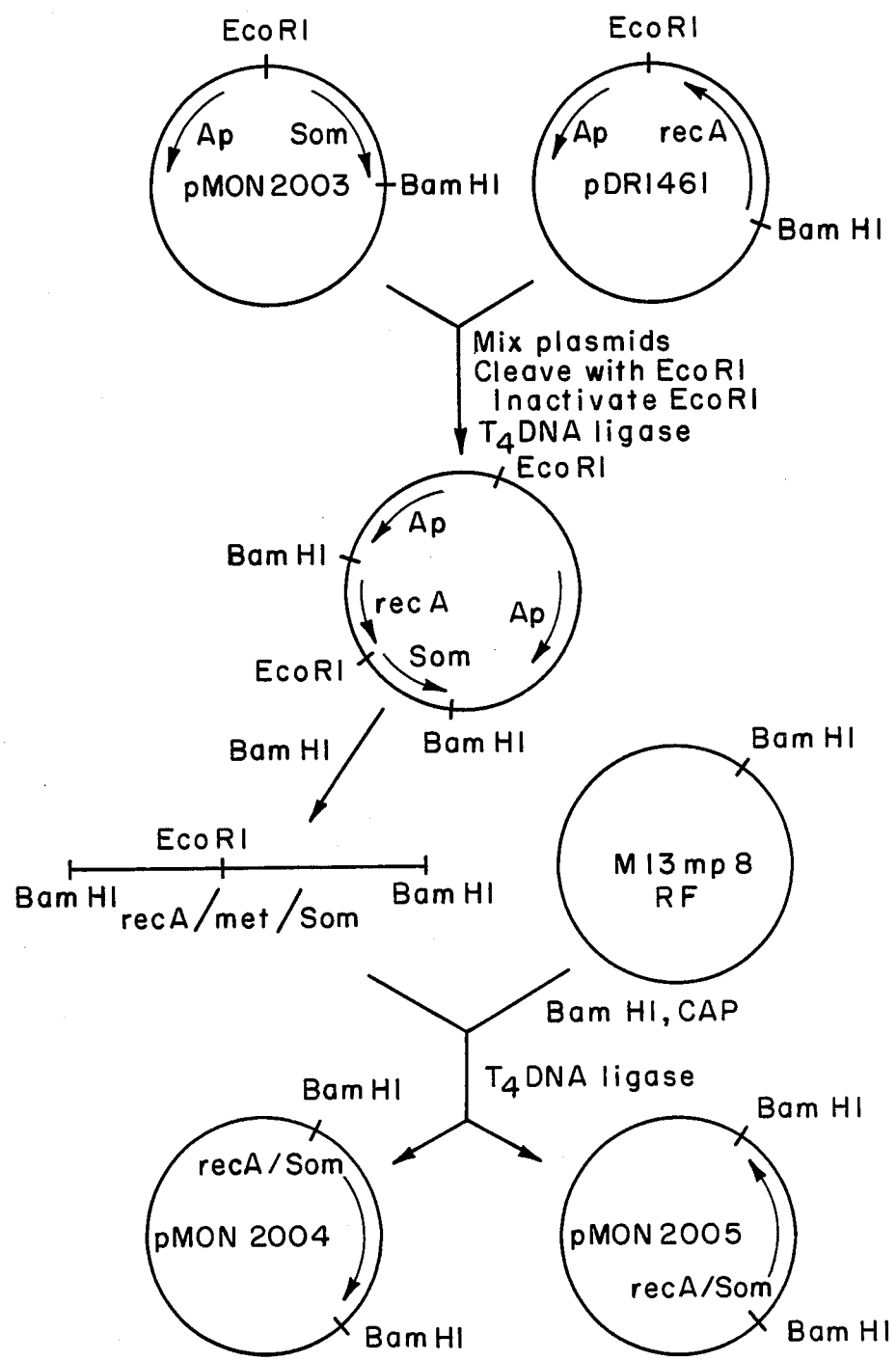
FIG. 3 illustrates the ligation of the recA promoter/operator and partial structural sequence to a somatostatin structural sequence to form a chimeric gene. The chimeric recA/som gene was isolated on a BamHI fragment, and that fragment was inserted into an M13 phage (in two different orientations) to create plasmids pMON2005 and pMON2004.

0.6 pmol of plasmid pDR1461 was mixed with 3.5 pmol of plasmid pMON2003. This mixture was cleaved with EcoRI, heated to inactivate the endonuclease, and precipitated with ethanol. The precipitate was resuspended and ligated with T4 DNA ligase in a volume of 20 ul. This created the chimeric recA/somatostatin gene with the methionine joint shown in Table I. Ligation was terminated by heat inactivation (5 minutes at 70° C.), NaCl was added to 50 mM and the reaction products were cleaved with BamHI endonuclease. This mixture was heat inactivated, ethanol precipitated, and resuspended in 20 ul of 10 mM Tris-HCl (pH 8.0), 1 mM EDTA. 3 ul of this mixture was ligated to 20 fmol of BamHI-digested, CAP-treated M13 mp8 DNA, in a volume of 15 ul. 5 ul aliquots of the resulting mixture were used to transform *E. coli* strain JM101 and the transformed cells were plated in agar containing IPTG (isopropyl-D-thiogalactopyranoside) and X-Gal (5-bromo-4-chloro-3-indolyl-B-D-galactopyranoside) by procedures as previously described by J. Messing, *Nucleic Acids Res.* 9,: 309–321 (1981) to detect phages containing cloned DNA inserts. Twenty-four large colorless plaques were screened for the presence of cells harboring M13 replicative form (RF) DNA containing a BamHI insert of 1.8 kb. Five clones of this type were recovered and the orientation of the 1.8 kb insert was determined by digestion with EcoRI. Plasmids (M13 RF DNA) having each orientation were designated as pMON2004 and pMON2005, as shown in FIG. 3. Three other clonal isolates were designated as pMON2006, 2007, and 2008, created by the same process. The expression of the recA/somatostatin fusion polypeptide by these plasmids is discussed in Example 7, below.

EXAMPLE 5

Construction of pMON2506 and 2505

Plasmid pMOB45 is a 10.5 kilobase plasmid having restriction sites for the restriction endonucleases EcoRI, BamHI and HindIII. It contains a temperature sensitive replicon, and genes for tetracycline resistance (Tc ®) and chloramphenicol resistance (Cm ®). Its construction is described by Bittner and Vapnek, *Gene* 15, 319–329 (1981).

1.7 pmol of plasmid pMON2005 was digested with BamHI and the reaction products were separated on a 5% polyacrylamide gel. The 1.8 kb fragment was recovered by electroelution. Ten percent of the recovered fragment (170 fmol) was ligated with 15 fmoles of DNA from plasmid pMOB45, which had been digested with BamHI and treated with CAP in a 15 ul reaction. 7.5 ul aliquots of the reaction were used to transform *E. coli* strain DB1443, and the transformation mixture was plated on chloramphenicol-containing Luria plates. Six Cm ® colonies were screened for plasmids bearing a 1.8 kb BamHI insert. The plasmids having this insert in each orientation were designated as pMON2505 and pMON2506, as shown in FIG. 4. The expression of the recA/somatostatin fusion polypeptide by these plasmids is discussed in Example 7, below.

EXAMPLE 6

Construction of pMON2507 and 2508

Plasmid pKO-1, described by McKenney et al., in *Gene Amplification and Analysis*, Vol. II, Chirkjian and Papas, eds., Elsevier Publ., 1981, was obtained from M. Rosenberg of the National Institute of Health. This plasmid is a derivative of pBR322 which contains a promoterless galactokinase (gal-K) gene located near a unique BamHI cleavage site.

Plasmid pKO-1M was constructed by the following steps. First, the single EcoRI site on that plasmid was destroyed by digesting the plasmid with EcoRI endonuclease, and then filling in the sticky ends using bacteriophage T4 DNA polymerase and all four deoxynucleotide triphosphates, then ligating together the resulting blunt ends. The plasmid resulting from these operations was designated pKO-1M1. This plasmid was then cut with the nuclease SmaI, and an oligonucleotide linker (GGAATTCC) having an EcoRI cleavage site was inserted at the SmaI site to form plasmid pKO-1M2. This plasmid was then digested with EcoRI and the multiple restriction site linker with EcoRI termini from phage M13mpF was inserted to produce plasmid pKO-1M.

Approximately 170 fmol of the 1.8 kb BamHI fragment of pMON2005 containing the recA/somatostatin gene fusion was ligated to 40 fmol of BamHI-digested, CAP-treated DNA from plasmid pKO-1M. 7.5 ul aliquots of the ligation mixture were used to transform *E. coli* strain N100K$^-$ cells according to the procedure described by McKenney et al. supra. Transformed cells were plated on ampicillin-containing galactose MacConkey's agar. Red and white Ap®️ colonies were screened for the presence of a 1.8 kb BamHI insert in the parent plasmid. Of those colonies with inserts, red colonies (gal$^+$) had the structure of pMON2507, and white colonies (gal$^-$) had the form of pMON2508 as shown in FIG. 5. The expression of recA/somatostatin fusion polypeptides by these plasmids is discussed in Example 7, below.

EXAMPLE 7

Expression of recA/somatostatin by various vectors

Five clonal isolates bearing plasmids pMON2004 through 2008 (M13 mp8 DNA, modified by the insertion of the recA/somatostatin chimeric gene as described in Example 4 and FIG. 3) were tested for production of somatostatin in the presence and absence of nalidixic acid. Control cells were infected with the unmodified M13 vector. *E. coli* cells, strain JM106 were grown to a Klett of 100 (Klett-Summerson colorimeter, green filter) in 2X YT broth at 37° C. Cultures were then split into halves, one of which was induced by the addition of freshly prepared nalidixic acid (10 mg/ml in 100 mM NaOH) to a final concentration of 50 ug/ml. Both cultures were allowed to grow for one hour at 37° C., then were harvested by centrifugation, resuspended in a solution of 5 mg/ml CNBr in 70% formic acid (which cleaves the recA/somatostatin polypeptide at the methionine joint shown in Table I to release the somatostatin sequence from the recA polypeptide) then tested by radioimmunoassay for the presence of somatostatin. The results of this test are presented in Table 3. Four of the five cultures showed production of somatostatin, which was strongly increased by nalidixic acid induction. One of the isolates, designated as pMON2007, did not express significant levels of somatostatin; this is believed to be the result of some loss of proper phasing between the joined segments.

TABLE 3

| | ng Somatostatin/ml of Culture Media | | | | | |
|---|---|---|---|---|---|---|
| | Vector (pMON #) | | | | | |
| | 2004 | 2005 | 2006 | 2007 | 2008 | mp8 |
| Uninduced | 15 | 11.5 | 11 | 0.16 | 13.8 | 0.17 |
| Induced | 310 | 255 | 310 | 0.22 | 295 | 0.285 |

*E. coli* cells (strain DB1443) containing plasmids pMON2506 or 2505 (described in Example 5 and FIG. 4) were cultured overnight in 2X YT broth at room temperature. This inoculum was diluted to 10 Klett in fresh 2X YT media and cultured at 40° C. for three hours to induce a high plasmid copy number. The cultures were then induced with nalidixic acid, as described above, for two or three hours. Cells were harvested by centrifugation, treated with CNBr in formic acid, then tested for somatostatin by radioimmunoassay. The results are shown in Table 4. Somatostatin production is two to three times greater than production by recA plasmids derived from M13 vectors, and about 1000 times greater than the reported expression of somatostatin under the control of a B-galactosidase promoter/operator region, described by Itakura et al, *Science* 198: 1056 (1977).

TABLE 4

| | ng of Somatostatin/ml of Culture Media | | |
|---|---|---|---|
| | Plasmid | | |
| | pMON2505 | pMON2506 | pMOB45 |
| Uninduced | 24 | 16 | <3 |
| 1 hr induction | 245 | 290 | <3 |
| 2 hrs induction | 510 | 520 | <3 |
| 3 hrs induction | 700 | 700 | <3 |

*E. coli* cells, strains N100K$^-$(recA$^-$) containing plasmid pMON2507 (described in Example 6 and FIG. 5) were grown to 150 Klett in 2X YT media, then split into halves. One of the cultures was then induced with nalidixic acid for 1 hour. Aliquots of each culture were harvested by centrifugation, treated with CNBr in formic acid, then tested for somatostatin by radioimmunoassay. The results, as shown in Table 5, indicate that the expression of the chimeric gene is strongly inducible in recA$^+$ host cells, but only weakly inducible in recA$^-$ host cells.

TABLE 5

| | ng Somatostatin/ml of Culture Media Determined by RIA | |
|---|---|---|
| Host Cell | Induced | Uninduced |
| DB1443 (recA$^+$) | 950 | 17.5 |
| N100K$^-$ (recA$^-$) | <3 | <3 |
| DB1443 (recA$^+$) (plasmid pKO-1M) | <1 | <1 |
| N100K$^-$ (recA$^-$) (plasmid pKO-1M) | <1 | <1 |

A comparison of galactokinase levels in recA$^+$ *E. coli* harboring pMON2507, or pMON2507 with an inserted recA transcription terminator which blocks transcription past the recA/somatostatin structural sequence, is presented in Table 6.

TABLE 6

| Construct | | Specific Activity of Galactokinase* |
|---|---|---|
| pMON2507 | (uninduced) | 29 |

TABLE 6-continued

| Construct | | Specific Activity of Galactokinase* |
|---|---|---|
| | (induced) | 139 |
| pMON2507 | (uninduced) | <1 |
| with transcription terminator | (induced) | <3 |

*p moles galactose-phosphate formed/minute/ug extract/ml

EXAMPLE 8

Fusion Polypeptides with recA Sequences of Varied Length

To determine whether the expression and accumulation of recA/somatostatin fusion polypeptides is sensitive to the length of the polypeptide, the Applicant constructed three plasmids having fused recA/methionine/somatostatin structural sequences of varying length, each of which was under the control of the recA promoter/operator region and 5' non-translated region. These plasmids are listed in Table 7, along with the length of the recA sequence and the quantity of somatostatin expressed by each plasmid.

Figure 6:
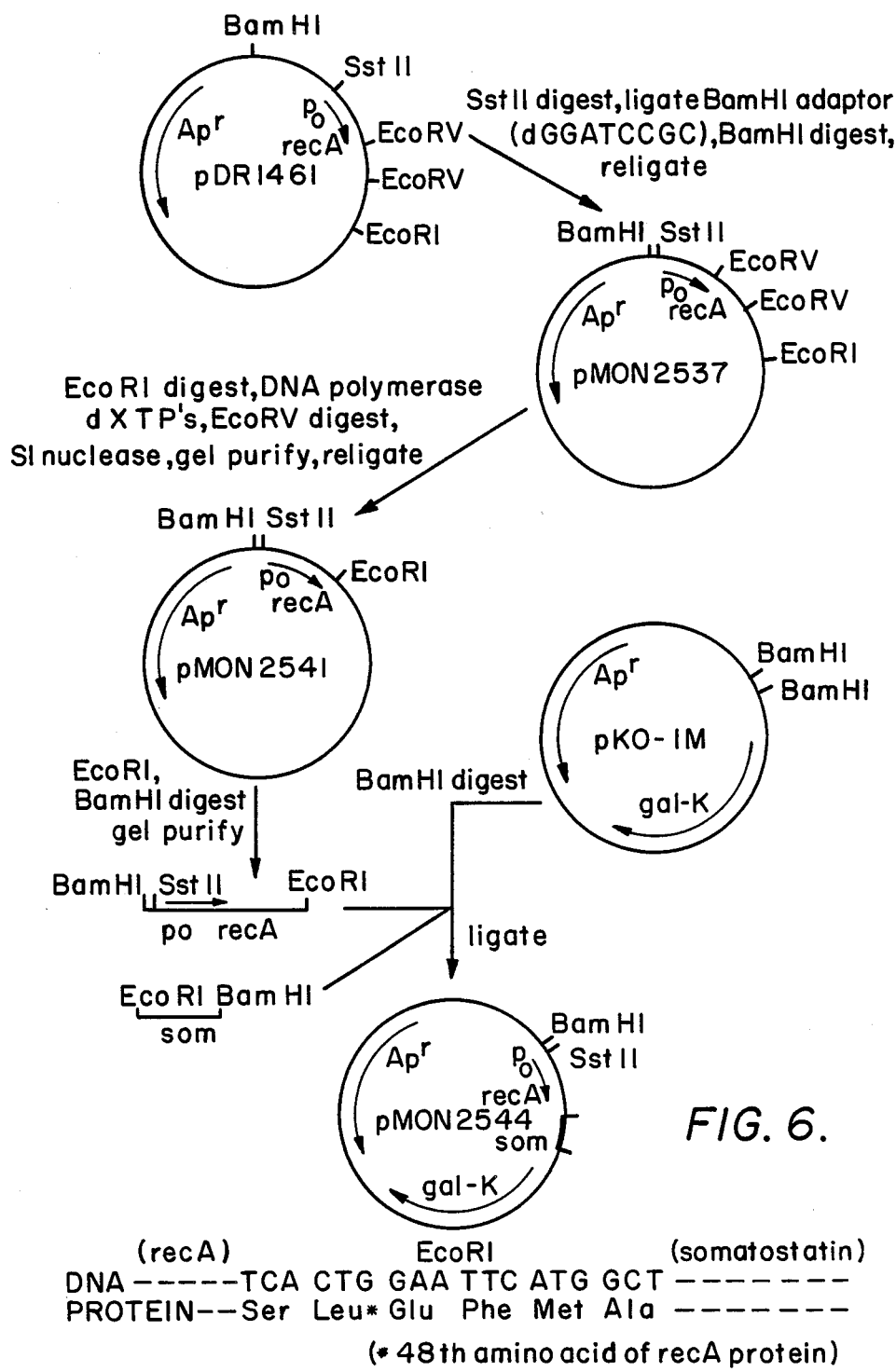
FIG. 6 illustrates the construction of pMON2544, which contains a recA/som gene that codes for 48 amino acids of recA.

To create pMON2544 (which has codons for 48 amino acids of the recA polypeptide, two additional codons which provide an EcoRI restriction site, the methionine junction codon, and the somatostatin codons), a derivative of pDR1461 was prepared in which the 800 bp BamHI to SstII DNA fragment preceding the recA promoter was deleted. As shown in FIG. 6, plasmid pDR1461 was restricted with SstII and ligated with a BamHI adaptor. This plasmid was digested with BamHI, diluted to remove the small fragment, and ligated, producing plasmid pMON2537. This plasmid was cut and treated with EcoRI and with DNA polymerase and deoxynucleotides to fill in the EcoRI cohesive termini, and then restricted with EcoRV and treated with nuclease S1 to remove the resulting single strands at the EcoRV restriction site. The vector fragment was then gel purified and ligated to itself to generate an EcoRI joint between the EcoRV site at the coding sequence for amino acid 49 of the recA gene and the EcoRI site of the pBR322 vector. These manipulations have the effect of converting the EcoRV site at the coding sequence for amino acid 49 into an EcoRI site in the proper phase to use for fusion with the synthetic somatostatin coding sequence. This truncated recA fragment (BamHI to EcoRI) was then used to construct a somatostatin expression vector by ligating it with both (1) the EcoRI-BamHI somatostatin fragment from plasmid pMON2003, described in Example 2, and (2) BamHI-cleaved plasmid pKO-1M. Products of this ligation which could render transformed E. coli N100 galK phenotypically galK+ had the structure denoted pMON2544 in FIG. 6. These plasmids have the recA:-somatostatin coding junction depicted in FIG. 6.

Figure 7:
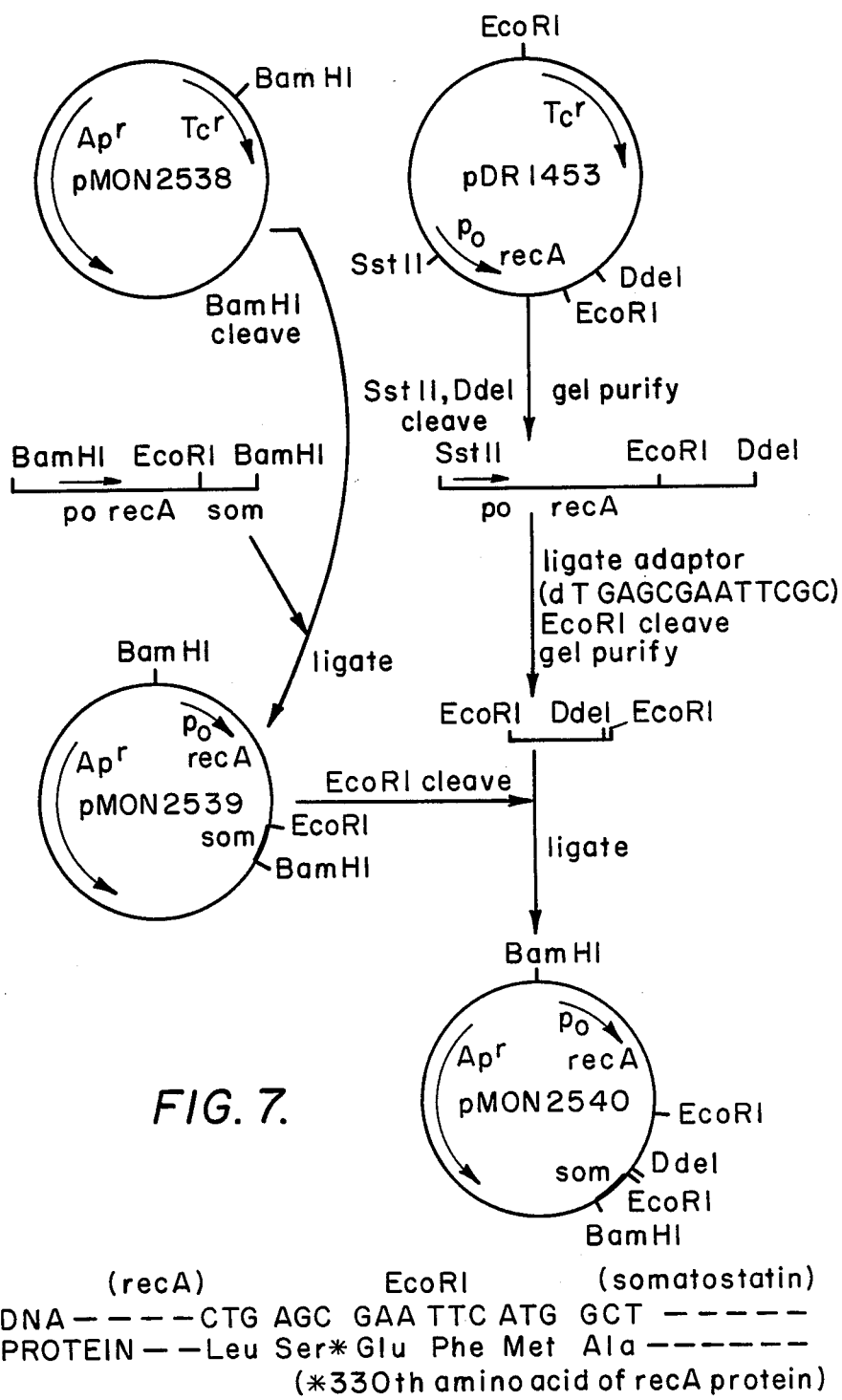
FIG. 7 illustrates the construction of pMON2539 and pMON2540, which contain recA/som genes that code for 260 and 330 amino acids of recA, respectively.

To create plasmid pMON2539 (which contains 260 recA codons followed by a methionine codon and the somatostatin codons), the 1.8 kb BamHI fragment containing the recA/somatostatin chimeric gene was isolated from plasmid pMON2004 (described in Example 4). This fragment was inserted into a pBR322 derivative, pMON2538, in which the original EcoRI site was removed, producing plasmid pMON2539, as shown in FIG. 7. Plasmid pMON2540 contains 330 recA codons, followed by two additional codons which provided an EcoRI restriction site, the methionine codon, and the somatostatin codons. To obtain this plasmid a DNA fragment containing recA codons 261 through 330 were inserted into the EcoRI site of plasmid pMON2539. This fragment was obtained by digesting plasmid pDR1453 (see Example 3) with EcoRI and DdeI. An oligonucleotide linker (d-TGAGCGAATTCGC) was annealed and ligated to this fragment, and the resulting mixture was cleaved with EcoRI to convert the DdeI terminus to an EcoRI terminus. The resulting fragment was inserted into the EcoRI site of pMON2539. A plasmid having an insert with the proper orientation was identified by means of an asymmetric HindII restriction site within the inserted fragment. This plasmid was designated as pMON2540, as shown in FIG. 7.

To test for expression of the various recA/somatostatin fusion polypeptides, E. coli DB1433 strains with plasmids pMON2544, 2539, or 2540 were cultured, induced with 50 ug nalidixic acid for 2 hours, harvested, treated with CNBr, and analyzed by RIA. The results, shown in Table 7, indicate that relatively high levels of somatostatin are expressed in the larger (260 and 230 amino acid carrier) fusion polypeptides, while considerably lower levels of expression resulted from the smaller (49 amino acid carrier) fusion polypeptide.

TABLE 7

| plasmid | recA amino acid residues | ng somatostatin/ml | ng somatostatin/mg protein |
|---|---|---|---|
| pMON2544 | 48 | 37.5 | 0.05 |
| pMON2539 | 260 | 562.5 | 1.26 |
| pMON2540 | 330 | 537.5 | 0.70 |

EXAMPLE 9

Comparison of recA and B-gal Carrier Polypeptides

As mentioned above, Itakura et al previously reported the expression of a fusion polypeptide containing the somatostatin sequence coupled to part of the B-gal polypeptide, in Science 198: 1056 (1977). This report referred to problems (such as plasmid instability) which limited the quantity of somatostatin that could be expressed and accumulated by E. coli cells containing plasmids with B-gal/somatostatin plasmids. The Applicant attempted to create similar plasmids, for three reasons: (1) to evaluate the extent of such problems; (2) to compare the B-gal promoter/operator system to the recA promoter/operator system, and (3) to compare B-gal to recA as a carrier protein for somatostatin. The results, described below, indicate that recA/ somatostatin chimeric genes are markedly superior to B-gal/-somatostatin chimeric genes for expression of somatostatin-containing fusion polypeptides by E. coli.

To construct the B-gal/somatostatin gene fusions, an EcoRI fragment of phage λplac 5 which contains the gene for B-gal and its control elements was inserted into the unique EcoRI site of pMON1004 as shown in FIG. 2. E. coli B-gal contains a total of 1021 amino acids; codons for the N-terminal 1005 amino acids are present on the DNA fragment. Loss of the C-terminal region (amino acids 1006-1021) results in the loss of enzymatic activity. The λplac EcoRI fragment was ligated to EcoRI-digested, CAP-treated pMON1004 and the products were used to transform the lac Z+ strain SR2. Colonies that contain the phage fragment insert were identified by their ability to form blue colonies on LB plates containing ampicillin and the chromogenic B-gal substrate, Xgal.

Transformation of strain SR2 with the pMON1004-λplac ligation mix yielded a high proportion of blue colonies on plates containing X-gal. However, the colonies were small. Attempts to demonstrate the presence of plasmids in culture grown from these colonies were unsuccessful in all but one isolate. The failure to detect λplac inserts at high frequency in either orientation is believed to reflect the instability of plasmids containing B-gal/somatostatin gene.

The reasons for the instability of plasmids with this gene are not clear. One possibility is that low level constitutive expression of the fusion products caused by repressor titration might be detrimental to the cells. If this were the case, then an increase in repressor concentration in the cells might stabilize the plasmid. To test this possibility, the ligation mixtures of pMON1004-λplac 5 were used to transform E. coli JM101 cells, which contain the I$^q$ allele of the lac repressor. The I$^q$ mutation results in 10-fold increase in the lac repressor concentration due to oversynthesis of repressor. Colonies containing the plac inserts were identified by their blue color when replica plated onto Luria agar plates containing Xgal and IPTG.

Figure 8:
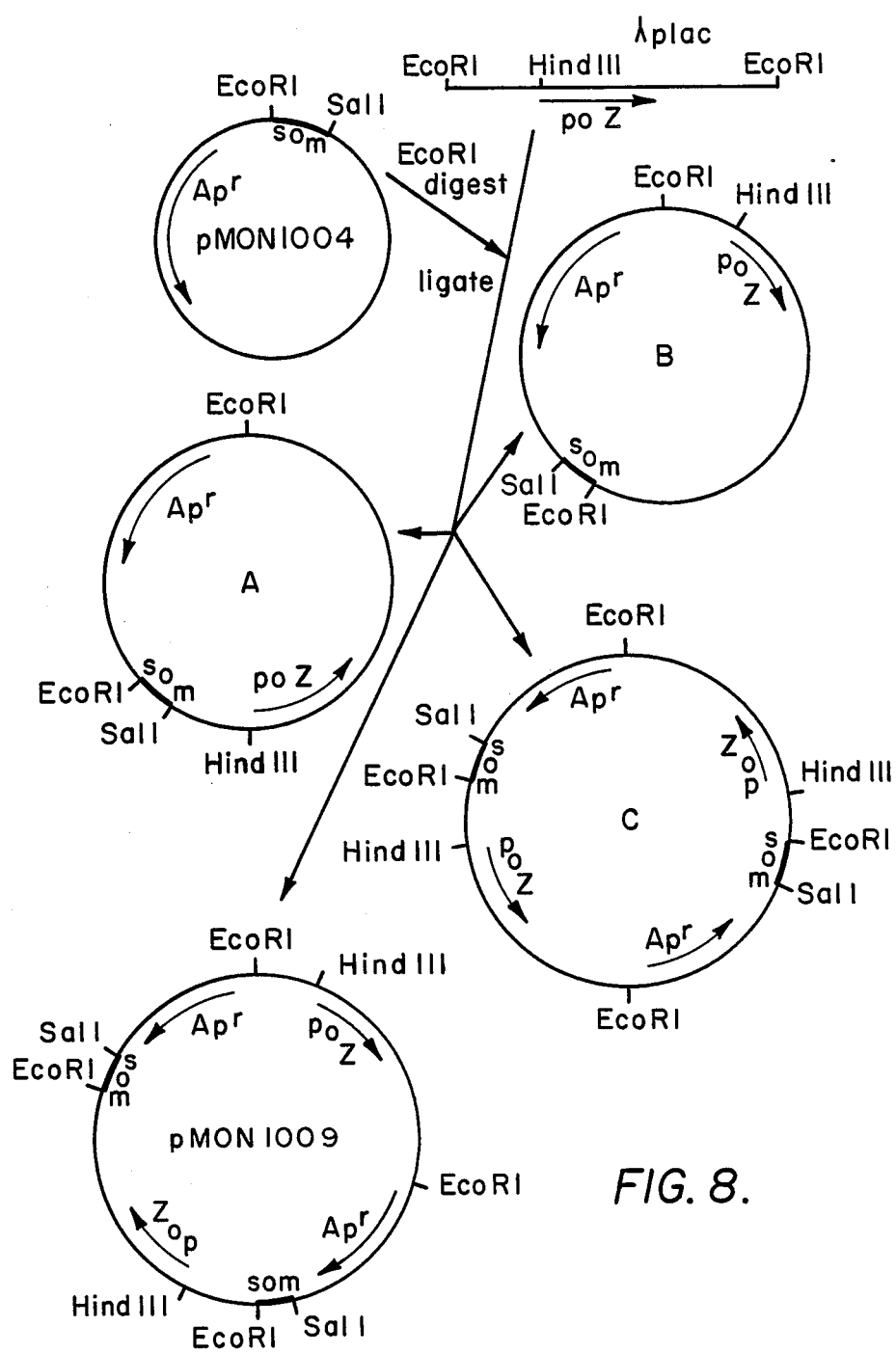
FIG. 8 illustrates various plasmids created in attempts to create B-gal/som fusion polypeptides.

In contrast to the results obtained in the SR2 strain, all transformants of JM101 showed the presence of stable plasmids. The orientation of the λplac insert in these isolates was determined by measuring the distance from the unique PstI site in the ampicillin resistance gene of the plasmid to the unique HindIII site in the plac fragment. Most of the 25 isolates examined showed incorporation of the plac fragment in the orientation depicted in plasmid A in FIG. 8. No isolates of the desired type B in FIG. 8, where the B-gal reads towards the somatostatin gene, were found; however, dimeric plasmids with structures depicted by C were found, none of which express B-gal/somatostatin. The absence of monomeric plasmids (type B structure) under conditions which yielded dimeric plasmids (which require tetramolecular ligations) indicates a strong selection against cells which contain plasmids that express B-gal/somatostatin. The only isolate that showed a correct B-gal/somatostatin fusion was a dimer, pMON1009, shown in FIG. 8. This plasmid has two plac inserts in head to tail orientation separated by two pBR327 2.7 kb fragments in head to head orientation with respect to each other. One of the B-galactosidase genes in this plasmid reads towards the somatostatin gene. All further experiments used pMON1009 as the source of B-gal/somatostatin fusion polypeptide.

Logarithmically growing cultures of JM101 containing plasmids A, C, and pMON1009 (shown in FIG. 8) were induced with 0.5 mM IPTG (controls were not induced) and assayed for the presence of somatostatin after CNBr cleavage, as described above. The results of these experiments are shown in Table 8.

TABLE 8

| Plasmid | Somatostatin, ng/ml of culture | |
|---|---|---|
| | uninduced | induced |
| pMON1004 | 0.2 | 0.2 |
| 6X | 0.2 | 0.2 |
| 7X | 0.2 | 0.2 |
| pMON1009 | 0.30 | 2.5 |
| | 0.35 | 3.1 |
| | 0.20 | 2.7 |
| | 0.25 | 2.5 |

The uninduced levels of somatostatin, measured by RIA, produced by pMON1009 is only slightly higher than that found in JM101 cells transformed with plasmids pMON1004, which contains the somatostatin structural sequence without a promoter. IPTG induction caused an 8- to 10-fold increase in the level of somatostatin in pMON1009 cultures but not in cells transformed with plasmids pMON1004, A or C. These results show that the somatostatin found in pMON1009-transformed JM101 cultures arises through transcription from the lac promoter of the B-gal/somatostatin chimeric gene in pMON1009. pMON1009 is maintained with reasonably high stability in JM101 and the same levels of somatostatin production were demonstrated in JM101 cells transformed with purified pMON1009.

When the B-gal/somatostatin fusion gene pMON1009 was excised by HindIII and SalI digestion and inserted into pBR327 or pBR322, the resultant plasmids produced somatostatin at levels comparable to pMON1009. However, no induction of B-gal/somatostatin peptides by IPTG was seen on gels. In addition, the 5.9 kb EcoRI-HindIII fragment of the B-gal gene in pMON1009 was cloned into the pBR327 between its EcoRI and HindIII sites, producing a plasmid similar to plasmid A in FIG. 8. High levels of B-gal size protein were not induced by this isolate in spite of the removal of somatostatin sequences. These results indicate that the B-gal/somatostatin gene in pMON1009 is transcribed at a rate much lower than the normal B-galactosidase gene.

The highest levels of somatostatin observed by the Applicant after diligent efforts to create B-gal/somatostatin fusion polypeptides were about 2.5 ng of somatostatin per ml of culture; this was about 4 ng of somatostatin per mg of protein. By comparison, the Applicant was able to create recA/somatostatin chimeric genes which expressed 900 ng of somatostatin per ml of culture, which was about 2000 ng of somatostatin per mg of protein.

An attempt to produce a chloramphenicol acetyl transferase (CAT)/somatostatin fusion peptide was made in the following manner. An EcoRI site was introduced near the BamHI site of the EcoRI-BamHI somatostatin fragment from pMON2003 by filling in the sticky ends produced by BamHI cleavage, followed by ligation of the oligonucleotide CCGGAATTCCGG (which codes for an EcoRI site) to the blunt end. This created a somatostatin fragment bounded by EcoRI termini. This fragment was ligated into EcoRI-cleaved pMOB45, which would create an in-frame fusion to the CAT gene, if the EcoRI fragment entered the plasmid in the proper orientation. Twenty four independent isolates which carried the somatostatin fragment inserted at the EcoRI site were tested for orientation (by means of the assymetric SalI site) and it was determined that none of the inserts had the desired orientation. Since the chances of all twenty-four of the inserts being inserted in the non-desired orientation is small, a metabolic process that strongly selected against cells containing plasmids with the insert in the desired orientation was presumed to occur.

EXAMPLE 10

Somatostatin Analogs

To further illustrate the use of the recA promoter/operator system for the production of heterologous polypeptides in bacteria, a series of coding segments for analogs of somatostatin were prepared and fused to recA in the same manner as the coding sequences for natural somatostatin, described above. Each such analog differed from somatostatin by the change of a single amino acid.

The somatostatin analogs thus prepared and tested contained the following amino acid substitutions:

TABLE 9

| Residue # | Analog | Natural |
| --- | --- | --- |
| 9 | alanine | lysine |
| 9 | arginine | lysine |
| 7 | alanine | phenylalanine |

| Fusion (recA:pp) | ng Somatostatin/ml of Culture Media (by RIA) |
| --- | --- |
| Natural somatostatin | 800 |
| Somatostatin analog alanine 9 | 160 |
| Somatostatin analog arginine 9 | 300 |
| Somatostatin analog alanine 7 | 2 |
| Control (no plasmid) | 2 | pp = polypeptide coding segment

EXAMPLE 11

Induction of recA/somatostatin

*E. coli* DB1443 cells with either: (1) no plasmids, (2) pMON2507, (3) pDR1461, or (4) pMON2012 were grown to 150 Klett in 2×YT media. The culture was divided into aliquots. Either 1 mg/ml mitomycin C or 50 mg/ml nalidixic acid was added to each aliquot. The aliquots were incubated for 2 hours at 37° C. One ml samples were taken, washed in 1 ml of 100 mM NaCl and 50 mM TrisHCl and repelleted. Samples were hydrolyzed overnight in 1 ml of 70% formic acid with 5 mg/ml CNBr, then lyophilized and analyzed by radioimmunoassay.

E coli B/r cells containing either (1) no plasmid, (2) pMON2507 or (3) pDR1461 were grown to 150 to Klett in M9 minimal media with 0.2% glucose. The culture was divided, and 50 mg/ml nalidixic acid was added to half of the culture. The other half was placed in a plastic petri dish and irradiated for 10 seconds with 1 J/m²/sec of ultraviolet radiation. The cultures were incubated for 2 hours at 37° C. Samples were treated and analyzed as described above.

One sample from each treatment described above was analyzed for total protein content by Lowry assay, using bovine serum albumin (BSA) as a standard, using absorption at 750 nm. The results were correlated with RIA activity to obtain the data shown in Table 10.

TABLE 10

| Cell type and treatment | ng of som/ ml of culture | ng of som/ ug of protein |
| --- | --- | --- |
| Control cultures | 4 | |
| DB1443 with pMON2507 | | |
| uninduced | 70 | 0.15 |
| nalidixic acid | 1750 | 3.93 |
| mitomycin C | 2500 | 7.62 |
| DB1443 with pMON2012 | | |
| uninduced | 62.5 | 0.14 |
| nalidixic acid | 1300 | 7.57 |
| mitomycin C | 2150 | 7.57 |
| B/r with pMON2507 | | |
| uninduced | 37.5 | 0.014 |
| nalidixic acid | 362.5 | 1.05 |
| ultraviolet | 400 | 1.29 |

EQUIVALENTS

Those skilled in the art will recognize, or may ascertain using no more than routine experimentation, numerous equivalents to the specific embodiments of this invention described herein. Such equivalents are within the scope of this invention.

I claim:

1. A double-stranded DNA cloning vector comprising, in phase from the 5' end to the 3' of the sense strand thereof:
   (a) a recA promoter/operator region;
   (b) a 5' non-translated region including a ribosomal binding site suitable for translation of a structural sequence in *E. coli* bacteria; and
   (c) a structural sequence capable of being translated into a fusion polypeptide in *E. coli*, wherein the fusion polypeptide comprises at least about 150 amino acid residues of a recA sequence coupled to a heterologous polypeptide sequence.

2. A cloning vector of claim 1 in which the heterologous polypeptide is somatostatin.

* * * * *